US008691249B2

(12) United States Patent
Schaefer et al.

(10) Patent No.: US 8,691,249 B2
(45) Date of Patent: Apr. 8, 2014

(54) PEELING CAPSULES

(75) Inventors: Jessica Schaefer, Hamburg (DE); Silke Weyland, Worms (DE)

(73) Assignee: Beiersdorf AG, Hamburg (DE)

( * ) Notice: Subject to any disclaimer, the term of this patent is extended or adjusted under 35 U.S.C. 154(b) by 785 days.

(21) Appl. No.: 12/441,553

(22) PCT Filed: Sep. 15, 2007

(86) PCT No.: PCT/EP2007/008051
§ 371 (c)(1),
(2), (4) Date: May 14, 2009

(87) PCT Pub. No.: WO2008/034565
PCT Pub. Date: Mar. 27, 2008

(65) Prior Publication Data
US 2009/0317431 A1    Dec. 24, 2009

(30) Foreign Application Priority Data
Sep. 22, 2006   (DE) .......................... 10 2006 044 942

(51) Int. Cl.
*A61K 8/02* (2006.01)
*A61K 9/48* (2006.01)

(52) U.S. Cl.
USPC ............................ 424/401; 424/451; 424/452

(58) Field of Classification Search
USPC ......................................... 424/401, 451, 452
See application file for complete search history.

(56) References Cited

U.S. PATENT DOCUMENTS

| 4,242,219 | A | * | 12/1980 | Bogerman et al. | 510/392 |
| 5,013,473 | A | * | 5/1991 | Norbury et al. | 424/452 |
| 5,089,269 | A | * | 2/1992 | Noda et al. | 424/456 |
| 5,866,145 | A |  | 2/1999 | Stavroff et al. | |
| 6,306,806 | B1 |  | 10/2001 | St. Lewis et al. | |
| 2003/0133900 | A1 | * | 7/2003 | McLaughlin | 424/70.22 |
| 2004/0052746 | A1 | * | 3/2004 | Tamareselvy et al. | 424/70.11 |
| 2006/0127427 | A1 | * | 6/2006 | Vernice et al. | 424/401 |

FOREIGN PATENT DOCUMENTS

| EP | 0 330 453 A2 | 8/1989 |
| JP | 63-185914 A | 8/1988 |
| WO | 00/04867 A2 | 2/2000 |
| WO | WO 00/04867 * | 2/2000 |
| WO | WO00/04867 * | 2/2000 |
| WO | 01/64166 A1 | 9/2001 |
| WO | 2005/020940 A1 | 3/2005 |
| WO | 2005/020949 A1 | 3/2005 |

OTHER PUBLICATIONS

English language abstract of 63-185914 A.

* cited by examiner

*Primary Examiner* — Brian-Yong Kwon
*Assistant Examiner* — Genevieve S Alley
(74) *Attorney, Agent, or Firm* — Abel Law Group, LLP

(57) ABSTRACT

A cosmetic peeling preparation which comprises a plurality of capsules. A capsule comprises a casing and a filling. The casing material is solid at 25° C. and selected from cosmetically conventional lipids, waxes, emulsifiers, natural polymers, synthetic polymers, and mixtures thereof. The filling comprises an oil or lipid mixture having a viscosity at 25° C. of from 3 to 50,000 mPas and one or more solid substances having an abrasive effect.

14 Claims, No Drawings

PEELING CAPSULES

BACKGROUND OF THE INVENTION

1. Field of the Invention

The invention relates to peeling capsules and dermatological peeling preparations in the form of capsules comprising a dimensionally stable capsule casing and a filling.

2. Discussion of Background Information

The epidermis is composed of different types of cells: the germ layer (stratum germinativum), the granular layer (stratum granulosum) and the horny layer (stratum corneum). In the germ layer new cells are formed by division which migrate permanently to the skin's surface. On the way there, in the granular layer, they keratinize and decay. These decayed horny cells as horny columns comprise most of the cells in the skin. The epidermis renews itself once within 28 days. Usually the dead horny cells are detached gradually unnoticed and by themselves.

On very stressed body parts, such as, e.g., hands, feet or knees, as well as in the case of very dry skin, there can be an increasing accumulation of horny scales, which are not detached by themselves and thus lead to unattractive, dull and even in part lacerated skin.

There are various ways of ridding the skin of these superfluous horny scales. On the one hand, there are various tools, such as pumice stones, washcloths or loofahs. On the other hand, it is widespread to rub the skin with loose granules, such as, e.g., sand, salt, sugar or wheat germ. Furthermore, there are cosmetic preparations, such as wash peelings, which usually contain plastic particles with an abrasive effect. In order to be able to easily remove these plastic particles from the skin again, surfactants are added to most wash peelings. However, these surfactants remove not only the plastic particles, but also endogenous lipids that are located on the skin, and thus often lead after use to a tightening and itching of the skin.

The tightening and itchy skin feeling can be avoided by adding oils or lipids to the cosmetic peeling preparation. One example of particularly regreasing peeling preparations are oil/salt mixtures.

Salt slurries in oil for use as a peeling preparation have been known to the consumer for some time (example: "Großmutters Hausmittel, neu entdeckt," ©2000 Reader's Digest, Verlag Das Beste GmbH, Stuttgart, Zürich, Vienna). Mixtures of this type are likewise commercially available as cosmetic finished products (example: Alessandro® Hands! Up Magic Manicure®). The fine salt particles in these mixtures over time settle to the bottom of the container and form a visible salt layer there. The mixing of the two phases can be very time-consuming and require a high expenditure of energy depending on the size of particles of the salt used. It is often not possible to achieve a uniform blending of the product, which means that the oil is used up more quickly. A virtually dry and solid salt layer is left behind on the bottom of the container, which can no longer be used.

Approaches to rectifying this situation emulsion capsules are presented in documents WO 00/04867 and U.S. Pat. No. 5,866,145.

Within the scope of this invention the problem of sedimentation is to be resolved, in that the salt slurry is integrated into a capsule as a single-use application.

Cosmetic capsules as a form of administration of cosmetic active substances—or only as preparation form with a unique application experience—are likewise known. They are described, for example, in documents WO 05/20940 and WO 05/20949 and referred to as emulsion capsules.

The disadvantage of emulsion capsules of this type is that the capsule casing is often smeared on the skin in large chunks in an unattractive manner.

SUMMARY OF THE INVENTION

The present invention provides a cosmetic peeling preparation which comprises a plurality of capsules. A capsule comprises a capsule casing and a capsule filling. The capsule casing material is solid at 25° C. and selected from cosmetically conventional lipids, waxes, emulsifiers, natural polymers, synthetic polymers, and mixtures thereof. The capsule filling comprises (i) an oil or lipid mixture having a viscosity at 25° C. of from 3 to 50,000 mPas and (ii) one or more solid substances having an abrasive effect.

In one aspect of the preparation, (i) may have a viscosity at 25° C. of from 1,000 to 8,000 mPas, e.g., from 2,000 to 4,000 mPas.

In another aspect, the capsule casing material may be solid or dimensionally stable up to a temperature of at least 35° C.

In another aspect, the waxes may comprise one or more of cetyl palmitate, cetyl rizinoleate, beeswax, hydrogenated cocoglycerides, methyl palmitate, candelilla wax, carnauba wax, paraffin wax, ceresine, ozocerite, myristyl myristate, tripalmitin, tribehenin, glyceryl palmitostearate, hydrogenated rapeseed oil, and $C_{15}$-$C_{40}$ alkylstearyl stearate. For example, the waxes may comprise one or more of ceresine and ozocerite.

In yet another aspect of the preparation, the capsules may be substantially spherical. For example, they may have an average diameter of from 5 mm to 50 mm, e.g., from 8 mm to 15 mm.

In a still further aspect, the average capsule volume may be from about 0.25 ml to about 25 ml and/or the average thickness of the capsules may be from 0.001 mm to 3 mm.

In another aspect, (ii) may comprises one or more of sea salt, rock salt, saline salt, and Himalaya salt and/or particles of one or more of viscose, cellulose, polypropylene, polyester, polyethylene terephthalate (PET), polytetrafluoroethylene (PTFE), aramid, nylon, Kevlar, polyvinyl derivatives, polyurethanes, polylactide, polyhydroxyalkanoate, polycarbonate, polystyrene, cellulose esters, and polyethylene, and/or particles of one or more of calcium sulfate, and calcium carbonate and/or one or more of encapsulated or unencapsulated crystals of calcium chloride, potassium chloride, magnesium chloride, and sugar, and silicates, sea sand, alum clays and/or one or more of crushed or ground wheat, flaxseed, rice, corn, almonds, nuts, nutshells, pumpkin seeds, caraway, crushed or ground natural sponges, and natural and synthetic waxes such as, e.g., one or more of rice bran wax, carnauba wax, jojoba wax, and beeswax.

In yet another aspect of the preparation, the volume ratio (i):(ii) may be from 70:30 to 40:60.

In a still further aspect, the grain size of (ii) may be from 40 μm to 2000 μm, e.g., less than 800 μm.

DETAILED DESCRIPTION OF THE INVENTION

It was not rendered obvious by the prior art that cosmetic peeling preparations in capsule form of a capsule casing wherein the capsule material is selected from the group of the cosmetically conventional lipids, waxes, emulsifiers, natural or synthetic polymers which are solid at 25° C. or the mixtures of one or more substances selected from the group of cosmetically conventional lipids, waxes, emulsifiers and natural or synthetic polymers, which mixtures are solid at 25° C. and a capsule filling of an oil or lipid mixture that at 25° C. has a viscosity between 3 and 50,000 mPas, preferably between 1000 and 8000 and very particularly preferably between 2000 and 4000 mPas, one or more solid substances having an abrasive effect would solve the problems of the prior art.

During use, the entire capsule is rubbed in, the casing as well as the filling. Through the solid substance or substances with abrasive effect in the filling, a peeling effect is achieved, the oils on the one hand provide a good gliding of the solid substance or substances with abrasive effect and on the other hand they have a regreasing effect.

Furthermore, the solid substance or substances with abrasive effect in the interior help in the disintegration of the capsule casing. The problem of the capsule casing that is hard to distribute, which is observed with emulsion capsules, could be clearly improved by the addition of the solid substance or substances with abrasive effect.

The waxes of the capsule casing form a protective film. After thorough rubbing in and distribution, any remaining residue can be washed away with water.

The property of the casing is advantageously characterized in that it melts on the skin when the preparation is rubbed in or distributed and/or becomes fully or partially liquid due to shearing forces and/or it is dissolved in the filling and/or the skin sebum lipids or by the mixing of inner phase and casing material and thus can no longer be perceived by the user as a separately present constituent of the preparation in addition to the filling.

Many terms such as "balls," "capsules," "capsule-form preparation" can basically be used to describe the capsules according to the invention, even if different meanings are assigned to these terms under some circumstances.

In general according to the invention a capsule is an object that is, for example, approximately round or ellipsoid, and clearly distinguishable from its surroundings, which with light pressure thus, for example, by grasping during removal from a packaging, does not change its shape or changes its shape only insignificantly. Within the scope of this disclosure this state of the capsule is also described as "dimensionally stable" or "solid."

However, other shapes of the capsules or the preparations are also conceivable according to the invention, as long as the claimed features of the capsule, the capsule casing and the filling are retained.

The capsules according to the invention have an average diameter of typically 5 to 50 mm, and are preferably approximately the size of a pea to the size of a cherry, thus approx. 8 to 15 mm in diameter. The capsules can thus be handled and applied individually.

The casing is advantageously made up of waxes such as ceresine, ozocerite, ester waxes, glyceride waxes and/or fatty alcohols as well as solid emulsifiers and mixtures thereof. In terms of origin, the waxes can be natural waxes, modified natural waxes, partially synthetic or fully synthetic.

The casing material according to the invention is preferably composed of waxes selected from the group of natural waxes, particularly preferably carnauba wax, candelilla wax, shellac wax, berry wax (*Rhus verniciflura*), hydrogenated vegetable oils, such as hydrogenated palm oil or rapeseed oil, beeswax, wool wax (eucerit), sunflower wax, jojoba wax mono-, di- and triglycerides of higher saturated fatty acids with 10-40 carbon atoms or mixtures thereof, particularly preferably glyceryl tripalmitate (Dynasan 116) and/or glyceryl stearate, Kahl wax 6447 (mixture of fatty acid esters and hydrocarbon polymer), glyceryl tribehenate (Syncrowax HRC)

higher saturated fatty alcohols, particularly preferably those with 14-30 carbon atoms, very particularly preferably stearyl alcohol and/or behenyl alcohol and/or cetyl alcohol synthetic esters, preferably $C_{16-36}$ alkylhydroxystearoyl stearate, stearyl stearate, cetearyl behenate, $C_{20-40}$ alkyl stearate, particularly preferably cetyl palmitate, methyl palmitate, myristyl myristate, polymer waxes, preferably polyethylene, polypropylene, polyvinyl ether, polydecene, particularly preferably polyvinylstearyl ether and hydrogenated polydecene, copolymers, particularly preferably those of ethylene and vinyl acetate, as well as polyvinyl pyrrolidone and hexadecene, hydrocarbons/paraffin waxes, particularly preferably cera microcristallina, paraffin wax, ceresine, ozocerite silicon waxes chemically modified waxes any mixtures of waxes from the listed groups.

Waxes which are particularly preferred according to the invention for producing the casing according to the invention are cetyl palmitate, beeswax, hydrogenated cocoglycerides, methyl palmitate, candelilla wax, carnauba wax, paraffin wax, ceresine, ozocerite, myristyl myristate, tripalmitin, tribehenin, glyceryl palmitostearate, hydrogenated rapeseed oil, $C_{15}$-$C_{40}$ alkylstearyl stearate and $C_{18-36}$ fatty acid triglyceride.

Within the context of the present disclosure a generic term which is sometimes used for fats, oils, waxes and the like is the expression "lipids," with which the person skilled in the art is entirely familiar. The terms "oil phase" and "lipid phase" are also used synonymously.

The internal oil phase of the formulations according to the invention is advantageously selected from the group of polar oils, for example from the group of lecithins and of fatty acid triglycerides, namely the triglycerol esters of saturated and/or unsaturated, branched and/or unbranched alkanecarboxylic acids with a chain length of from 8 to 24, in particular 12 to 18, C atoms. The fatty acid triglycerides can, for example, be chosen advantageously from the group of synthetic, semi-synthetic and natural oils, such as, for example, cocoglyceride, olive oil, sunflower oil, soybean oil, peanut oil, rapeseed oil, almond oil, palm oil, coconut oil, castor oil, wheat germ oil, grapeseed oil, thistle oil, evening primrose oil, macadamia nut oil and the like.

For the purposes of the present invention, further advantageous polar oil components can also be chosen from the group of esters of saturated and/or unsaturated, branched and/or unbranched alkanecarboxylic acids with a chain length of from 3 to 30 C atoms and saturated and/or unsaturated, branched and/or unbranched alcohols with a chain length of from 3 to 30 carbon atoms, and from the group of esters of aromatic carboxylic acids and saturated and/or unsaturated, branched and/or unbranched alcohols with a chain length of from 3 to 30 C atoms. Such ester oils can then advantageously be chosen from the group octyl palmitate, octyl cocoate, octyl isostearate, octyl dodecyl myristate, octyldodecanol, cetearyl isononanoate, isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, stearyl heptanoate, oleyl oleate, oleyl erucate, erucyl oleate, erucyl erucate, tridecyl stearate, tridecyl trimellitate, and synthetic, semi-synthetic and natural mixtures of such esters, such as, for example, jojoba oil.

In addition, the oil phase can be chosen advantageously from the group of dialkyl ethers and dialkyl carbonates, advantageous are, for example, dicaprylyl ether (Cetiol OE) and/or dicaprylyl carbonate, for example that available under the trade name Cetiol CC.

It is also preferred to choose the oil components from the group isoeicosane, neopentyl glycol diheptanoate, propylene glycol dicaprylate/dicaprate, caprylic/capric/diglyceryl succinate, butylene glycol dicaprylate/dicaprate, $C_{12-13}$-alkyl lactate, di-$C_{12-13}$-alkyl tartrate, triisostearin, dipentaerythrityl hexacaprylate/hexacaprate, propylene glycol monoisostearate, tricaprylin, dimethyl isosorbide. It is particularly advantageous if the oil phase of the formulations according to the invention has a content of $C_{12-15}$-alkyl benzoate or is composed entirely thereof.

Any mixtures of such oil and wax components can also be used advantageously for the purpose of the present invention.

In addition, the oil phase can likewise advantageously also comprise non-polar oils, for example those which are chosen from the group of branched and unbranched hydrocarbons and hydrocarbon waxes, in particular mineral oil, vaseline (petrolatum), paraffin oil, squalane and squalene, polyolefins, hydrogenated polyisobutenes and isohexadecane. Among the polyolefins, polydecenes are the preferred substances.

The oil phase can also advantageously have a content of cyclic or linear silicone oils or be composed entirely of such oils, although it is preferred to use an additional content of other oil phase components apart from the silicone oil or the silicone oils.

Silicone oils are high molecular weight synthetic polymeric compounds in which silicon atoms are joined via oxygen atoms in a catylated and/or reticular manner and the remaining valences of silicon are saturated by hydrocarbon radicals (mostly methyl groups, more rarely ethyl, propyl, phenyl groups, etc.). Systematically, the silicone oils are referred to as polyorganosiloxanes. The methyl-substituted polyorganosiloxanes, which constitute the most important compounds of this group in terms of amount and are characterized by the following structural formula $$H_3C-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_n-\underset{\underset{CH_3}{|}}{\overset{\overset{CH_3}{|}}{Si}}-CH_3$$

are also referred to as polydimethylsiloxane or dimethicone (INCI). Dimethicones are available in various chain lengths and with various molecular weights.

Particularly advantageous polyorganosiloxanes for the purposes of the present invention are, for example, dimethylpolysiloxanes [poly(dimethylsiloxane)], which are available, for example, under the trade names Abil 10 to 10 000 from Th. Goldschmidt. Also advantageous are phenylmethylpolysiloxanes (INCI: Phenyl Dimethicone, Phenyl Trimethicone), cyclic silicones (octamethylcyclotetrasiloxane and decamethylcyclopentasiloxane), which are also referred to as cyclomethicones in accordance with INCI, amino-modified silicones (INCI: Amodimethicone) and silicone waxes, e.g., polysiloxane-polyalkylene copolymers (INCI: Stearyl Dimethicone and Cetyl Dimethicone) and dialkoxydimethylpolysiloxanes (Stearoxy Dimethicone and Behenoxy Stearyl Dimethicone), which are obtainable as various Abil wax grades from Th. Goldschmidt. However, other silicone oils can also be used advantageously for the purposes of the present invention, for example cetyldimethicone, hexamethylcyclotrisiloxane, polydimethylsiloxane, poly(methylphenylsiloxane).

The oils that can be used for the internal oil phase, can also be used as advantageous additives for the casing material.

The preferred solid substance with abrasive effect is crystalline sodium chloride. But also sea salt, rock salt and saline salt as well as Himalaya salt.

However, it is also advantageous to use alternatively or additionally solid substances with abrasive effect chosen from the group of solid abrasive particles from all organic and inorganic solids on a natural or synthetic basis.

Fillers preferred according to the invention come from the group of inorganic or organic silicon compounds.

Of the inorganic silicon compounds, the phyllosilicates are particularly preferred. Of these, kaolin, talc and mica are particularly preferred.

Furthermore, the preferred inorganic silicon compounds include the spherical particles organically modified on the surface.

Of these, polymethylsilsesquioxane and hydrophobically modified aerosils, such as, e.g., Aerosil R 972 are particularly preferred.

The organic silicon compounds include siloxane elastomers and siloxane resins. Of these the KSP types from Shin Etsu and trimethylsiloxysilicate are particularly preferred.

Further fillers preferred according to the invention come from the group of spherical particles. An average particle diameter of less than 20 µm is particularly preferred. Furthermore, spherical particles of organic origin are also preferably selected.

Furthermore, spherical particles are preferred with an average particle diameter of less than 10 µm. Particularly preferred thereof are Nylon-12, which is sold, e.g., as SP-501 or SP-500 by Kobo. Furthermore polymethyl methacrylates are preferred, which are sold, e.g., under the trade name Covabead LH 85 by LCW.

Furthermore starch derivatives are preferably used. Particularly preferred thereof are aluminum starch octenylsuccinate, corn starch or sodium cornstarch octenylsuccinate.

It is advantageous according to the invention if the preparations are characterized in that they contain 0.001% by weight to 10% by weight, preferably 0.5% by weight to 5% by weight, in particular 1-4% by weight based on the total weight of the preparations, of one or more fillers.

Advantageous capsule fillings are characterized by proportions by volume of
Liquid oil or liquid lipid mixture to
One or more solid abrasive substances
which are selected from the range of from 70:30 to 40:60.

For the production of the capsule form preparation according to the invention the casing and the filling are initially produced separately from one another. The covering of the filling with the casing material, regardless of the composition of the filling material or the casing, can be carried out in various ways.

For example, the filling material can be frozen and then immersed in melted casing material, whereby a solid, closed casing is formed on the filling material.

However, hollow balls can also be casts from melted casing material, which balls are filled with filling material optionally by a hole in the ball wall. Subsequently the hole is closed by a plug of casing material.

Another possibility of the production is via the so-called one-shot method. Casing material and filling material are thereby cast simultaneously. The casting machine meters both masses from the divided reservoir through a concentric ring nozzle into a blister form. First the casing mass starts via the annular gap and then the filling follows with a short delay via the inner nozzle. The finished capsule can thus be cast in one step. This method is the preferred production method according to the invention.

It is also possible to first cast half hollow balls, to then fill them, to match them and subsequently by thermal treatment to fuse the two hollow balls to one another. Furthermore, two hemispheres of this type can be produced, wherein one or both have a hole for subsequent filling, then are fused to form a hollow ball, and subsequently are filled through the filling hole, which is then closed as described above.

It is advantageous according to the invention, although not mandatory, to sugar coat the peeling capsules according to known methods. Advantageously according to the invention, the coating material is selected from the group of the sugars conventionally used for this purpose, but also conventional dragee coatings, e.g., on the basis of polymethacrylates or methyl cellulose or a salt crust can be used.

Polymers can be applied to the casing to improve storage stability and breaking resistance. Suitable polymers are cellulose ethers, polyvinyl pyrrolidone, polyacrylates or polymethacrylates, as well as Eudragit.

Furthermore, it can be advantageous to cover the capsules with polishing waxes or hard waxes. These include above all shellac wax, carnauba wax or beeswax as well as further lac waxes.

Sugar coating means to cover a core with sugar layers. Nowadays other covering materials are used increasingly frequently. The applied layer either of sugar (=classic sugar dragee) or of another film former (=film tablets). The layer is usually dyed and can optionally also contain other substances in order to change the properties of the finished drug form in the desired manner (odor, taste . . . ).

Sugar coating is the classic coating method, i.e., the covering of the cores with sugar solutions. High production costs, the difficulties of automating the process and the long production time of up to a week per batch mean this method is being increasingly replaced by the film tablet.

In the case of cold sugar coating, the sugar solution is applied at normal room temperature, in the case of hot sugar coating the heated sugar syrup is used (approx. 50-60° C.).

The process is carried out in mushroom mixers in which the cores are started rolling by the rotation of the drums. The sugar coating liquid is added and gradually covers the cores. At the same time they are carefully dried (hot air or UV radiators). In the case of heat sensitive substances the drying can also be carried out by the addition of cool air.

The process is continued until a sufficiently thick and stable layer has formed around the core. This can take up to 50 sugar coating operations. The cores thereby undergo an increase in size and volume.

Sugar coating process in detail:

Impregnation
To protect the sugar coating liquid from penetrating to the core; e.g., with shellac solutions or polymerizates.

Covering
For mechanical protection and for preparation for the application. Covering syrup contains binders (PVP, cellulose, etc.) in addition to sugar.

Application (up to 50 times)
The application is the actual sugar coating process. Is repeated until the desired thickness has been achieved.

Coloring
For coloring dye is added to the last application layer (1-3%).

Smoothing
The smoothing syrup is applied in order to remove irregularities. Slow drying is important, therefore no supply of heat.

Polishing
To improve the appearance, it is allowed to run with oil or polishing wax in special drums lined with felt without application of heat.

Quick Sugar Coating

Quick sugar coating corresponds in its main operating steps to the sugar coating described above, The time saving is realized in that a layer thickness lower by 70% to 90% is accepted. Furthermore, sugar coating emulsions are used for sugar coating. Dragees can be produced in a few hours in this manner.

The following Examples illustrate the preparations in capsule form according to the present invention. Unless otherwise indicated, the percentages refer to the total weight of the preparations.

FORMULA EXAMPLES

Casing Material

| I. | |
|---|---|
| C18-36 fatty triglycerides | 12.2% |
| Hydrogenated cocoglycerides | 60.96% |
| Caprylic/Capric acid triglycerides | 12.2% |
| Cyclomethicone | 12.2% |
| Silica Dimethylsilylate | 2.44% |
| II. | |
| Isopropyl stearate | 47.17% |
| Glyceryl stearate | 1% |
| Polyethylene | 10% |
| Silica Dimethylsilylate | 5% |
| Triceteareth-4 Phosphate | 0.3% |
| Cetyl alcohol | 36.5% |

Filling Material

| III. | |
|---|---|
| Jojoba oil | 50% |
| Sodium chloride | 50% |
| IV. | |
| Stearyl alcohol | 0.25% |
| Beeswax | 0.25% |
| C18-36 fatty acid triglycerides | 2.75% |
| Paraffin oil | 46.55% |
| Perfume | 0.2% |
| Sea salt | 50% |

-continued

| V. | |
|---|---|
| Cetyl alcohol | 10% |
| Caprylic/Capric triglycerides | 40% |
| Sodium chloride | 50% |

Production

Example I with IV

Heat $C_{18-36}$ fatty acid triglycerides, hydrogenated cocoglycerides, capric/caprylic triglycerides and cyclomethicone to 80° C. Subsequently add silica dimethylsilylate to the melted lipid mixture while stirring.

Likewise melt stearyl alcohol, beeswax, C18-36 fatty acid triglycerides and paraffin oil and mix with sea salt.

Casing material and filling material are cast in one step to form a capsule using the one-shot method.

Subsequently the capsules are sugar coated in a mushroom mixer with a sugar solution or wax dispersion.

Production

Example II with III

For the casing material isopropyl stearate, glyceryl stearate, triceteareth-4 phosphate and cetyl alcohol are heated to 80° C. Subsequently while stirring mix silica dimethylsilylate and polyethylene into the melted lipid mixture.

For the filling mix jojoba oil and cooking salt in a ratio of 1:1.

Casing and filling material are cast in one step to form a capsule using the one-shot method.

Subsequently, the capsules are sugar coated in a mushroom mixer with a sugar solution or wax dispersion.

Production

Example I with V

Heat $C_{18-36}$ fatty acid triglycerides, hydrogenated cocoglycerides, caprylic/capric triglycerides and cylcomethicone to 80° C. Subsequently while stirring add silica dimethylsilylate to the melted lipid mixture.

Likewise melt cetyl alcohol and capric/caprylic triglycerides and mix with sodium chloride.

Casing material and filler material are cast to form a capsule in one step using the one-shot method.

Subsequently the capsules are coated in a mushroom mixer with a sugar solution or wax dispersion.

What is claimed is:

1. A cosmetic peeling preparation comprising a plurality of capsules, wherein a capsule comprises a capsule casing and a capsule filling, a capsule casing material being solid at 25° C. and being selected from cosmetically conventional lipids, waxes, emulsifiers, natural polymers, synthetic polymers, and mixtures thereof, and a capsule filling comprising (i) an oil or lipid mixture having a viscosity at 25° C. of from 3 to 50,000 mPas and (ii) one or more solid substances having an abrasive effect wherein the solid substances are selected from the group consisting of sea salt, rock salt, saline salt, Himalaya salt, calcium sulfate, calcium carbonate, encapsulated or unencapsulated crystals of calcium chloride, silicates, sea sand, alum clays, crushed of ground wheat, flaxseed, rice, corn, almonds, nuts, nutshells, pumpkin seeds, caraway, crushed or ground natural sponges, rice bran wax, carnauba wax, jojoba wax, beeswax, particles of one or more of viscose, polyester, polyethylene terephthalate (PET), polytetrafluoroethylene (PTFE), aramid, nylon, Kevlar, polyvinyl derivatives, polyurethanes, polylactide, polyhydroxylkanoate and polycarbonate.

2. The preparation of claim 1, wherein (i) has a viscosity at 25° C. of from 1,000 to 8,000 mPas.

3. The preparation of claim 1, wherein (i) has a viscosity at 25° C. of from 2,000 to 4,000 mPas.

4. The preparation of claim 1, wherein the capsule casing material is solid or dimensionally stable up to a temperature of at least 35° C.

5. The preparation of claim 1, wherein the waxes comprise one or more of cetyl palmitate, cetyl rizinoleate, beeswax, hydrogenated cocoglycerides, methyl palmitate, candelilla wax, carnauba wax, paraffin wax, ceresine, ozocerite, myristyl myristate, tripalmitin, tribehenin, glyceryl palmitostearate, hydrogenated rapeseed oil, and $C_{15}$-$C_{40}$ alkylstearyl stearate.

6. The preparation of claim 1, wherein the waxes comprise one or more of ceresine and ozocerite.

7. The preparation of claim 1, wherein the capsules are substantially spherical.

8. The preparation of claim 7, wherein the capsules have an average diameter of from 5 mm to 50 mm.

9. The preparation of claim 7, wherein the capsules have an average diameter of from 8 mm to 15 mm.

10. The preparation of claim 1, wherein an average capsule volume is from about 0.25 ml to about 25 ml.

11. The preparation of claim 1, wherein an average thickness of capsule casings is from 0.001 mm to 3 mm.

12. The preparation of claim 1, wherein a volume ratio (i):(ii) is from 70:30 to 40:60.

13. The preparation of claim 1, wherein a grain size of (ii) is from 40 μm to 2000 μm.

14. The preparation of claim 1, wherein a grain size of (ii) is less than 800 μm.

* * * * *